United States Patent [19]

Walt

[11] Patent Number: 5,114,864
[45] Date of Patent: May 19, 1992

[54] FIBER OPTIC SENSORS, APPARATUS, AND DETECTION METHODS USING FLUID ERODIBLE CONTROLLED RELEASE POLYMERS FOR DELIVERY OF REAGENT FORMULATIONS

[75] Inventor: David R. Walt, Lexington, Mass.

[73] Assignee: Trustees of Tufts College, Medford, Mass.

[21] Appl. No.: 409,462

[22] Filed: Sep. 19, 1989

Related U.S. Application Data

[63] Continuation-in-part of Ser. No. 294,175, Jan. 6, 1989, abandoned, which is a continuation-in-part of Ser. No. 878,128, Jun. 25, 1986, Pat. No. 4,822,746, and Ser. No. 305,176, Feb. 2, 1989, which is a continuation of Ser. No. 878,128.

[51] Int. Cl.[5] .................. G01N 21/62; G01N 21/63; G01N 21/64
[52] U.S. Cl. .................. 436/528; 422/82.05; 422/82.07; 422/82.08; 436/531; 436/172; 436/800; 436/805; 435/808; 385/12; 385/13
[58] Field of Search .............. 436/528, 166, 172, 800, 436/805; 422/82.07, 82.08, 82.05, 901; 424/426; 350/96.1, 96.2; 385/12, 13

[56] References Cited

U.S. PATENT DOCUMENTS

| | | | |
|---|---|---|---|
| 4,219,334 | 8/1980 | Schluter et al. | 436/166 |
| 4,387,164 | 6/1983 | Hevey et al. | 436/166 |
| 4,577,109 | 3/1986 | Hirschfeld | 422/82.07 |
| 4,898,734 | 2/1990 | Mathiowite et al. | 424/426 |
| 4,929,561 | 5/1990 | Hirschfeld | 422/82.07 |
| 4,929,562 | 5/1990 | Anderson et al. | 436/172 |

Primary Examiner—David Saunders
Assistant Examiner—Christopher L. Chin
Attorney, Agent, or Firm—David Prashker

[57] ABSTRACT

An improved fiber optic sensor, sensing apparatus, and methods for making optical determinations are provided. The fiber optic sensor employs a fiber optic strand to convey light energy and at least one polymer matrix comprising a fluid erodible, continuous release polymer and a releasable reagent formulation able to react with a molecule or analyte of interest. The optic sensors and sensor construction has been demonstrated to be accurate, precise, and of long duration.

12 Claims, 3 Drawing Sheets

FIBER OPTIC SENSORS, APPARATUS, AND DETECTION METHODS USING FLUID ERODIBLE CONTROLLED RELEASE POLYMERS FOR DELIVERY OF REAGENT FORMULATIONS

RESEARCH SUPPORT

The research for the present invention was supported by a grant from the Environmental Protection Agency through the Tufts Center for Environmental Management.

CROSS-REFERENCES

This application is a continuation-in-part of application Ser. No. 294,175 filed Jan. 6, 1989, now abandoned which is a continuation-in-part of application Ser. No. 878,128 filed Jun. 25, 1986; and this application is also a continuation-in-part of application Ser. No. 305,176 filed Feb. 2, 1989 which is a continuation of application Ser. No. 878,128 filed Jun. 25, 1986, now U.S. Pat. No. 4,822,746.

FIELD OF THE INVENTION

The present invention is concerned with optical sensors and optical sensing apparatus utilizing colorimetric or fluorometric techniques as qualitative and quantitative detection systems; and is particularly directed to fiber optic sensors utilizing continuous release polymeric delivery systems capable of delivering unused sensing ligands and reagents over long periods of time for optical determinations.

BACKGROUND OF THE INVENTION

The science and instrumentation of spectroscopy as developed over the last century has become increasingly expanded and specialized as the various methods and applications of analysis came into existence. Today, spectroscopy has been divided into individual and distinctly different methods and instrumentation systems for: ultraviolet and visible spectrophotometry; fluorescence and phosphorescence spectrophotometry; flame emission and atomic absorption spectrometry; atomic emission spectroscopy; infrared spectrophotometry; raman spectroscopy; nuclear magnetic resonance spectroscopy; electron spin resonance spectroscopy; refractometry and interferometry; and various others. Of these, the optical sensors and optical sensing detection systems utilizing the ultraviolet and visible absorption methods and the fluorescence and phosphorescence excitation and emission systems are perhaps the best known and commonly utilized.

The essentials of an ultraviolet/visible spectrometry instrumentation system utilize the principles of absorption photometry; and comprise, in its simplest forms, a light energy source, focusing optics, an unknown or standard sample cuvette, a wavelength isolation device, and a detector with amplifier and readout system. From an engineering standpoint, it is desirable that this type of absorption photometry system be detector limited - that is, the limiting factor should be the noise generated by the detector. Anything that can be done to increase signal levels at the detector is therefore desirable. The measure of performance is usually defined as precision, or photometric accuracy. In terms of construction, one recognizes the differences between single-beam and double-beam light paths; and whether the photometer module is a direct reading or employs a balance circuit. Other available instrumentation features include double monochromatation and dual wavelength systems.

In comparison, fluorescence and phosphorescence is a physical phenomenon based upon the ability of some molecules to absorb and then emit light. With these molecules, the absorption of light energy (photons) at specified wavelengths is followed by the emission of light from the molecule of a longer wavelength and at a lower energy state. Such emissions are called fluorescence if the emission lifetime is relatively short-lived, typically a rate of from $10^{-9}$ to $10^{-7}$ seconds. Phosphorescence lifetimes usually are longer and fall within the range from $10^{-4}$ to 10 seconds. The most striking difference between the two emission forms are the conditions under which each type of photoluminescence is observed. Fluorescence is usually seen at moderate temperature in the liquid solution. Phosphorescence is seen in rigid media, usually at very low temperatures.

A simple generalized instrument suitable for fluorescence and phosphorescence spectrophotometry usually comprises a source of light energy; a primary filter or excitation monochromator; a sample cell; a secondary filter or emission monochromator; a photodetector; and a data readout device. In contrast to ultraviolet/visible instrumentation, two optical systems are necessary. The primary filter or excitation monochromator selects specific bands or wavelengths of radiation from the light source and directs them through the sample in the sample cell. The resultant emission or luminescence is isolated by the secondary filter or emission monochromator and directed to the photodetector which measures the intensity of the emitted radiation. For observance of phosphorescence, a repetitive shutter mechanism is required.

For more complete and detailed information, the following publications and references are provided, the text of which are expressly incorporated by reference herein: Willard, Merritt, Dean, and Settle, *Instrumentation Methods Of Analysis*, 6th edition, Wadsworth Publishing Company, Belmont, Calif., 1981; Joseph R. Kakowicz, *Principles Of Fluorescence Spectroscopy*, Plenum Press, New York, 1983; Skoog and West, *Fundamentals Of Analytical Chemistry*, 4th edition, Saunders College Publishing, 1982.

A more recent event has been the development of fiber optic sensors and instrumentation systems utilizing ultraviolet, visible, and/or fluorometric photometry techniques. Such fiber optic sensors and sensing apparatus are fast becoming established analytical tools for remote and in-situ optical sensing determinations. The development of fiber optic sensors and their applications are illustrated by the following publications: Angel, S. M., *Spectroscopy* 2:38-48 (1987); Hilliard, L. A., *Analytical Proceedings* 22:210-224 (1985); Boisde et al., *Talanta* 35:75-82 (1988); Wolfbeis, O. S., *Pure & Appl. Chem.* 59:663-672 (1987); Seitz, W. R., *Anal. Chem.* 56:16A-34A (1984); and Seitz, W. R., *CRC Critical Reviews In Analytical Chemistry* 19:135-173 (1988).

Regardless of the light energy system and photometric basis employed, an ideal optical sensor must have the ability to measure the concentration of an analyte continuously over the entire range of changes in the optical properties of the sensing reagent. To date, this sensor ability has been based on the availability of suitable, long-lasting, reversible chemistries and reagents. The systems are thus based and dependent upon the ability of the reagent to first associate and then disassociate reversibly with the specific analyte—a requirement which has eliminated many colorimetric and fluorometric compositions and reactive ligands from being used in such sensors because these compositions are irreversible in their reactions. Accordingly, because many ultraviolet, visible, phosphorescent, and fluorescent compositions form a tightly binding complex with the analyte of interest or utilize reagents which generate an irreversibly colored or fluorescent adduct product for reaction with the analyte of interest, these compositions and photometric techniques have been generally avoided and deemed inappropriate for use with fiber optic sensors [see for example: U.S. Pat. No. 4,666,672; Vo-Dinh et al., *Appl. Spectros.* 41:235-738 (1987); Sutherland et al., *Clin. Chem.* 30:1533-1538 (1984); and Tromberg et al., *Anal. Chem.* 59:1226-1230 (1987)].

In those limited numbers of optic probes utilizing irreversible chemistries, these probes may be employed if they operate in an integrating mode; however, they must be replenished frequently with fresh sensing reagent ligands because of the irreversible nature of their reaction with the analyte to be detected Clearly, therefore, a fiber optic sensor which releases irreversible reagents and ligands reactive with an analyte of interest and which does not require frequent replenishment of reagents and provides accurate and reliable modes of delivery would be recognized and appreciated by ordinary practitioners within this art as a major improvement and substantive advance in this field.

SUMMARY OF THE INVENTION

The present invention, in its essence, provides a fiber optic sensor for optical determinations of a test fluid, this sensor comprising:

a housing with a securing means to hold a fiber optic strand, said housing comprising a reservoir chamber of determinable configuration and interior spatial volume;

at least one polymeric matrix positioned within said interior spatial volume of said reservoir chamber, said polymeric matrix comprising a fluid erodible, continuous release polymer and a releasable reagent formulation able to react with a molecule of interest in the test fluid;

a fiber optic strand positioned proximal to said polymeric matrix within said reservoir chamber, said fiber optic strand being able to convey light energy into and out of said interior spatial volume of said reservoir chamber; and flow communication means for the test fluid into and out of said interior spatial volume of said reservoir chamber.

Other aspects of the present invention provide a fiber optic sensing apparatus for making optical determinations; and methods for making optical determinations using the fiber optic sensor and the fiber optic sensing apparatus.

DETAILED DESCRIPTION OF THE FIGURES

The present invention may be more easily and completely understood when taken in conjunction with the accompanying drawing, in which.

DETAILED DESCRIPTION OF THE PREFERRED EMBODIMENTS

The present invention is an improvement in fiber optic sensor design and instrumentation systems which utilize prepared continuous release polymeric matrices for the controlled release and delivery of reagent formulations which after release are able to react reversibly or irreversibly with a specific molecule or analyte of interest. The improved fiber optic sensor is expected and intended to be used broadly in many different fields of spectrometry including ultraviolet, visible, and near infrared absorption photometry and with fluorescent and phosphorescent emission systems. All the presently known colorimetric or fluorometric phenomena, mechanisms of action, techniques, and applications can be employed directly with the various embodiments of the present invention.

All embodiments of the present invention encompass fiber optic chemical sensors which are based upon and utilize releasable reagent ligands or formulations which have been initially trapped and immobilized within a fluid erodible, continuous release polymer composition to form a prepared polymeric matrix. This preparatory technique is simple, straightforward, and reliable; and it overcomes the major limitation of using only reversible reagents and indicating systems when constructing fiber optic sensors.

There are only four essential components forming the improved fiber optic sensor comprising the present invention. These are: a reservoir chamber of determinable configuration; interior spatial volume of the chamber; at least one polymeric matrix positioned within the interior spatial volume of the reservoir chamber; a fiber optic strand positioned proximal to the polymeric matrix within the reservoir chamber; and flow communication means for a test fluid into and out of the interior spatial volume of the reservoir chamber.

Figure 2:
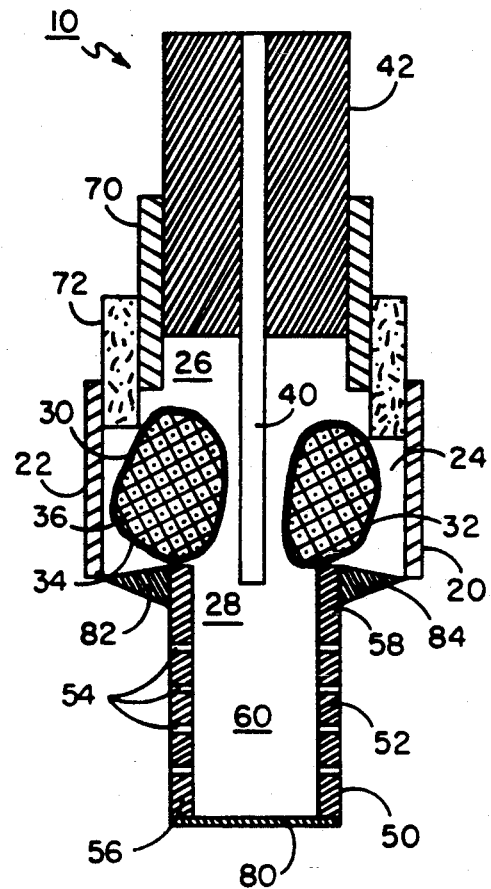
FIG. 2 is a cross-sectional view of a preferred embodiment of the fiber optic sensor comprising the present invention.

A preferred, specific embodiment of the improved fiber optic sensor is provided by FIG. 2. This embodiment is constructed as a long-lasting pH fiber optic sensor providing a controlled release of pH-sensitive fluorescent dyes upon contact with a test fluid. The fluorescent dyes have been incorporated into ethylene-vinyl acetate (hereinafter "EVA") copolymers and are released slowly from the polymeric matrix upon contact with any aqueous solution. This specific embodiment is described in complete detail and empirically evaluated in the experiments described hereinafter. However, the construction of this pH sensor will effectively serve now to describe the essential components generally as required for all embodiments of the present invention regardless of specific characteristics, capabilities, uses, or applications.

As seen in FIG. 2, the fiber optic sensor 10 comprises the four required elements of a reservoir chamber 20, polymeric matrices 30 and 32, a fiber optic strand 40, and flow communication means seen here as the hollow, conduit member 50. The reservoir chamber 20 seen in cross-sectional view, is a Teflon tube (preferably 3/16 inch inner diameter and ¼ inch outer diameter). The reservoir chamber 20, therefore has a single side wall 22, an interior spatial volume 24, and open portals 26 and 28 respectively. Within the interior spatial volume 24 lie polymeric matrices 30 and 32. Each polymeric matrix comprises a continuous release polymer 34 and a releasable reagent formulation 36 able to react irreversibly (in this instance) with a molecule of interest. Positioned through the open portal 26 and proximal to the polymeric matrices 30 and 32 is a glass fiber optic strand 40 having a plastic coating 42. This glass fiber 40 was cleaved with a carbide tip to ensure a smooth surface, washed in concentrated sulfuric acid, and then rinsed with distilled water before being positioned as shown. The conduit member 50 is positioned adjacent to the other open portal 28. In the embodiment of FIG. 2, the conduit member 50 is seen in cross-sectional view and is a Teflon tube (preferably 1/16 inch inner diameter and ⅛ inch outer diameter) having a single side wall 52 and a plurality of apertures 54 perforating the side wall proper. The distal end 56 of the conduit member 50 is sealed in this embodiment preferably using Parafilm 80 to make a fluid-tight closure. The proximal end 58 of the member 50 is similarly sealed using Parafilm 82,84 to the side wall 22 of the reservoir chamber 20. In this manner, the proximal end 58 is positioned adjacent to and sealed fluid-tight to the reservoir chamber 20 such that the perforated tube-like internal volume 60 is in direct and uninterrupted flow communication with the interior spatial volume 24 of the reservoir chamber 20.

In the illustrated embodiment, the fiber optic strand 40 is held in position and secured adjacent to the open portal 26 via tube sections 70,72 respectively. It will be recognized that this is merely one form of secure positioning for the fiber optic strand 40. The tube section 70, seen in cross-section, is preferably a capillary tube and is inserted into tube section 72 which is itself then inserted into and is retained in position by the side wall 22 of the reservoir chamber 20.

In actual use, the embodiment illustrated by FIG. 2 is employed with a liquid containing at least one specific molecule or analyte of interest. Because of the varying mechanisms of actions associated with colorimetric, fluorometric, and other known detection systems and techniques, it is not always necessary or useful for the reagent formulation to react directly with the analyte of interest. Rather, the reagent formulation once released may irreversibly react with a variety of other molecules which have been described and termed absorbers, proto-absorbers, and/or absorption complexes within U.S. Pat. No 4,822,746, the text of which is expressly incorporated by reference herein. Accordingly, the reagent formulation may react with either the true analyte or with another molecule of interest which is present within a test fluid, preferably a liquid aqueous solution. By the embodiment illustrated in FIG. 2, the test liquid is introduced into the fiber optic sensor by fluid passage through the apertures 54 of the conduit member 50 whereby the perforated internal volume 60 provides a fluid flow pathway into and out of the internal spatial volume 24 of the reservoir chamber 20. The presence of a test liquid within the internal spatial volume 24 acts to erode the polymeric matrices 30 and 32 such that the reagent formulation 36 is released continuously into the liquid within the reservoir chamber 20. The released reagent formulation is then able to react irreversibly (in this instance) with the molecule or analyte of interest such that the subsequent introduction of light energy into the reservoir chamber via the fiber optic strand 40 allows the user to make optical determinations and measurements colorimetrically and/or fluorometrically.

Although the embodiment of FIG. 2 utilizes Tygon and Teflon tubing as the preferred mode of construction for the reservoir chamber and the conduit member, any durable and resilient material or composition may be employed in forming the requisite components. All that is required is that the reservoir chamber be of determinable configuration and interior spatial volume. Similarly, it is necessary only that the flow communication means provide reliable conduits for the entry and egress of the test fluid from the interior of the reservoir chamber. Such flow communication means include porous membranes, perforated discs, and any other material or construct having tiny holes through which a fluid may pass. Accordingly, there are no restrictions or limitations whatsoever to the actual dimensions, shapes, flow designs, or integrating constructions which may be useful or operable. To the contrary, all these matters are deemed to be simply items of personal convenience and choice for the user which will vary greatly with the intended application and use circumstances. There are no paramount or decisive parameters or factors beyond those previously described herein for either the reservoir chamber or the flow communication means elements.

The use of optical fiber strands for detection purposes and within fiber optic sensors is well known in this art. Such glass fibers are described in: U.S. Pat. No. 4,577,109; and in Milanovich et al., "Novel Optical Fiber Techniques For Medical Application," published in *Proceedings Of The SPIE* 28th Annual International Technical Symposium On Optics And Electroptics, volume 494 (1984). In general, light from a light energy source is used to illuminate the distal end of the optical fiber strand, the light having a predetermined wavelength. The light energy is carried by the optic fiber strand along its length and dispensed from the proximal end adjacent the reservoir chamber for illumination with radiant light energy. The composition of the fiber strand is preferably glass but may be comprised of other materials as further developments in the fiber strand area occur. Any and all of these innovations regarding the optic fiber strand may be usefully employed for purposes of practicing the present invention without limitation.

The polymeric matrices useful within the present invention comprise fluid erodible, continuous release polymers, and a releasable reagent formulation able to react irreversibly (or reversibly) with a prechosen molecule or analyte of interest. Continuous release polymers which are erodible by liquids, preferably aqueous solutions, and releasable reagent formulations useful as ligands for optical determinations are conventionally known. A representative listing of erodible, continuous release polymers is provided by Table I and a representative listing of reagent formulations of diverse composition and properties is provided by Table II.

Table I: ERODIBLE CONTINUOUS RELEASE POLYMERS

Polyanhydrides (copolymers and homopolymers)
polysebacic acid
poly(p-carboxyphenoxy)propane
poly(p-carboxyphenoxy)hexane
polydodecanoic acid poly-1,4-plienylenediproprionic acid
poly-isophthalic acid Vinyl Polymers (copolymers and homopolymers)

ethylene vinyl acetate copolymer
polyvinylpyrrolidone
polyvinyl alcohol

Polyacrylamides poly-2-hydroxyethyl methacrylate

Polyglycolic Acids

Table II: REAGENT FORMULATIONS

Indicator Compounds and Dyes absorbers
protoabsorbers
absorption complexes
chromophoric compounds
chromogenic compounds
fluorophoric compounds
fluorogenic compounds Labelled Immunological and Immunochemical Compositions labelled antigens
labelled haptens
labelled antibodies and antibody fragments Enzyme System Components and Compositions enzymes and zymogens
enzyme substrates and substrate analogues
cofactors Fluid erodible polymers able to provide for the sustained release of macromolecules such as polypeptide hormones, polysaccharides, antigens, antibodies, and enzymes have been described in the scientific literature [Chasin et al., BioPharm. Mfg. 2:33-41 (1988); Langer, R., Chemtech. (12):98-105 (1982); Langer, R., Meth. Enzymol. 73:57-73 (1981); Rhine et al., J. Pharm. Sci. 69:265-270 (1980); Langer, R. and J. Folkman, Nature 263:797-799 (1976). All of these references are expressly incorporated by reference herein.

Similarly, the releasable reagent formulations may be selected from a wide and diverse range of compositions and properties. The releasable ligands include: known indicator compounds useful within ultraviolet, visible, fluorescent, phosphorescent, and other well defined optical systems and methods. Accordingly, these include the known colorimetric compositions known as absorbers, protoabsorbers, absorption complexes; chromophoric and chromogenic compositions; and fluorophoric and fluorogenic compounds—all of which are known and described in the relevant scientific and industrial literature. In addition, the reagent formulation released from the polymeric matrix may also have other attributes and capabilities such as specific binding properties. Accordingly, such reagent formulations include all the conventionally known labelled immunological compositions including labelled antigens, haptens, and other antibody or cellular immunological and/or immunochemical components. In addition, there are many applications where the components of known enzyme systems are useful as the releasable reagent formulations. Accordingly, these include specific enzymes of various and divergent specific activity, their specific enzyme substrates and/or substrate analogues, and the requisite cofactors necessary for the enzyme reaction to proceed. In addition, recognizing that the listing of Table II is merely representational and illustrative of the range and variety of formulations able to be immobilized within the prepared polymeric matrix, any and all other compositions, ligands, and chemical structures which have value and utility as an irreversible or reversible binding indicator by which to make an optical determination - in quantitative or qualitative terms using any known mechanism of action or technique—are all deemed to be within the scope of the present invention.

To demonstrate the utility and efficacy of the improved fiber optic sensor comprising the present invention, a variety of experiments and empirical data will be described hereinafter. It will be expressly understood, however, that these experiments and empirical results are merely descriptive of the various embodiments comprising the present invention as a whole; and serve merely to illustrate some of those situations and applications in which the present invention may be usefully employed. None of the experimental models, empirical data, or conclusions are deemed to be restrictive of the present invention in any form or use; to the contrary, it will be recognized and appreciated that these experiments merely demonstrate the variety of applications and the range of effective parameters one may expect to be in effect when employing the present invention.

EXPERIMENTS AND EMPIRICAL DATA

Materials

Ethylene-vinyl acetate copolymer (40% by weight vinyl acetate, Elvax 40) in pellet form, was obtained from duPont Corporation, Wilmington, Del. 8-hydroxypyrene-1,3,6-trisulfonic acid, trisodium salt (HPTS) was purchased from Molecular Probes, Eugene, Oreg. Sulforhodamine 640 (SR640) was purchased from Exciton, Dayton, Ohio. Teflon tubes were obtained from Cole-Parmer, Chicago, Ill.

Apparatus

Two different instrumentation systems were used in the two experimental approaches described below. The first system [described previously in Munkholm et al., Anal. Chem. 58:1427-1430 (1986)]employs a 488 nm argon-ion laser as the excitation source. Light is conducted through a series of lenses and filters into an optical fiber strand (Corning Core Guide glass NA (numerical aperture)=0.28). The fluorescence is conducted back through the same fiber strand and reflected by a dichroic mirror to a photomultiplier tube. The intensity of the fluorescence is measured as a function of emission wavelength using a photoncounting detection system (Pacific Instruments, Model 126).

Figure 1:
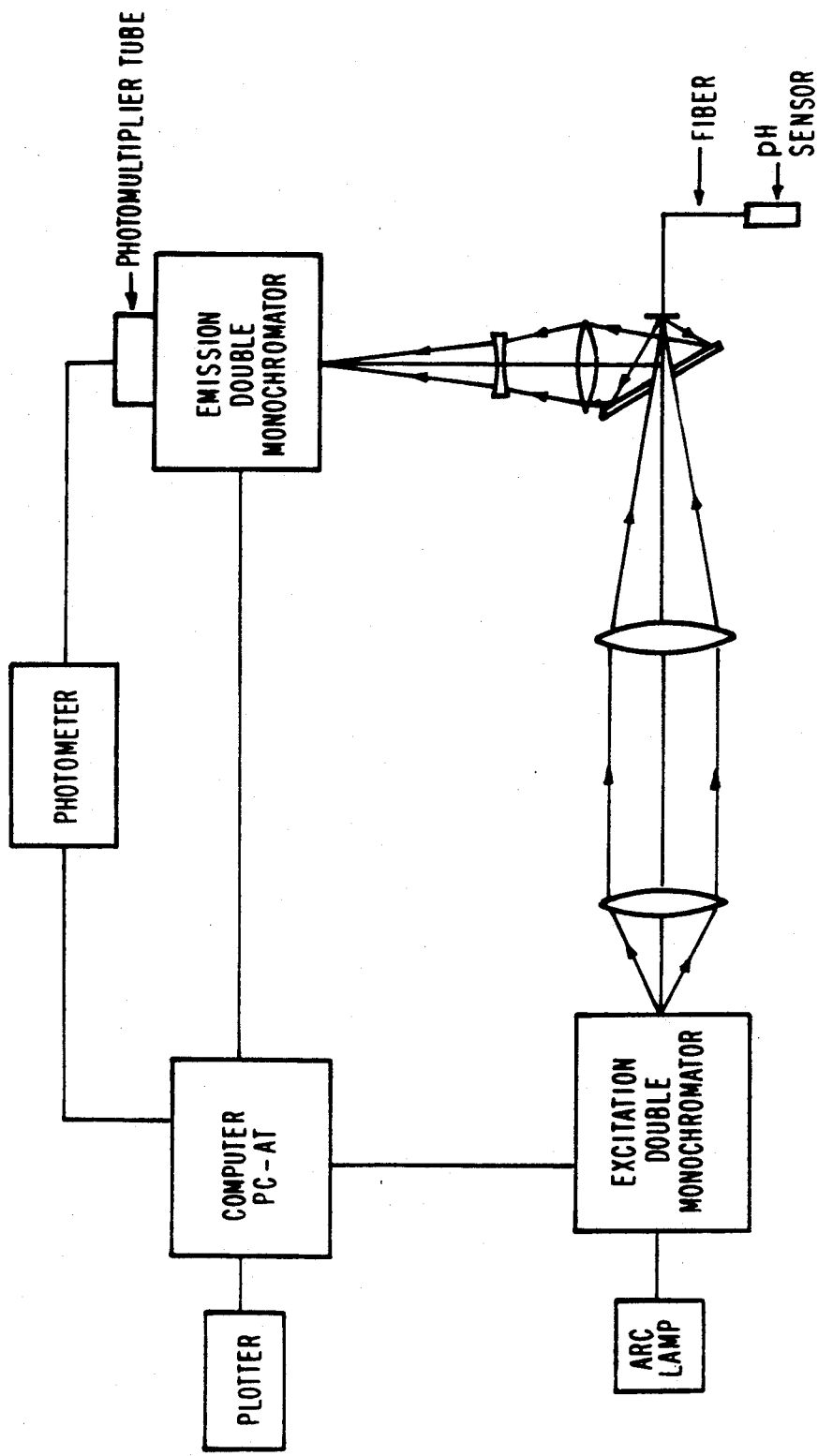
FIG. 1 is a schematic representation of a variable wavelength optical system.

The second variable wavelength optical system is schematically shown in FIG. 1. This system can be used to measure fluorescence intensity at different excitation wavelengths at a fixed emission wavelength and consists of four basic components: a variable wavelength light source for excitation; an optical system for conducting light into the sensor and to the detector; an emission detection system; and computer control and data acquisition system.

The excitation light source consists of a 75 watt high pressure Xenon arc lamp (Osram Company) which gives a continuous spectrum from 190 nm to 750 nm and a Spex 1680 0.22 m double monochromater for selecting any specified wavelength light. The use of a double monochromater ensures low stray light levels in the excitation. The optical system consists of lenses and mirrors that focus the excitation light onto the fiber, retrieve the emission light from the fiber and focus it onto the entrance slit of the emission detection system. The emission detection system is comprised of a second Spex 1680 0.22 m double monochromater with a 300 lines/mm grating and a RCA 31034A-02 photomultiplier tube. The detected signal is then processed by a photometer. Finally, a PC-AT with an AD (analog to digital) and DA (digital to analog) board is used to acquire and display the data, and to control the movements of the stepping motors in the excitation and emission spectrometers.

Sensor Construction

A cross-sectional view of a pH sensor 10 based on the polymeric continuous-release delivery system is shown in FIG. 2. One end of a glass fiber (200/250 um) was cleaved with a carbide tip to ensure a smooth surface, washed in concentrated sulfuric acid, and rinsed with distilled water. To prepare the sensor, the fiber strand was first inserted into a 1.5 cm long Teflon capillary tube 70 with an inside diameter (I.D.) of 1/32", and an outside diameter (O.D.) of 1/16". This tube 70 was then inserted into a 1 cm Tygon tube 72 having an I.D. of (I.D. 1/16" and O.D. of 3/16". This Tygon tube 72 was then connected to a reservoir chamber 20 made of another Teflon tube having an I.D. of 3/16" and O.D. of ¼". Lastly, a third Teflon tube 50 (I.D. 1/16", O.D. ⅛"), having many holes 54 (0.25-0.36 mm) drilled through its side wall 52, was sealed at its distal end 56 with Parafilm; and also wrapped with Parafilm at the proximal end 58 such that it fits snugly into the portal 28 of the reservoir chamber. These holes allow the exchange of solutions on both sides of the conduit member 50. The sensor containing polymeric matrices 30 and 32 was filled with buffer before sealing. No bubbles were introduced in the sensing region. All pH measurements were performed in phosphate-citric acid buffers.

Polymeric Matrix Preparation

Ethylene-vinyl acetate copolymer (EVA) pellets were first washed at least three times in distilled water with constant stirring The EVA pellets were then extracted in a Soxhlet extractor with high quality acetone for at least three days. The EVA pellets were then quickly removed from the paper thimble at the end of the extraction while the acetone was still hot. Finally, the EVA pellets were dried in a dessicator under house vacuum for at least a week. Drying was complete when all acetone had evaporated.

The EVA copolymer was dissolved in methylene chloride to give a 10% w/v solution. A weighed amount of 8-hydroxypyrene-1,3,6-trisulfonic acid (HPTS) was added to 15 mL of the polymer solution in a glass vial to give a dye loading of 33%. In the case of the HPTS and sulforhodamine 640 (SR640) mixture, a one to one ratio was employed, and the total loading in the polymer was 33%. Each prepared mixture was vortexed to yield a uniform suspension. After vortexing, the prepared mixture was poured quickly into the center of a glass mold (5×5×z2 cm), which had been cooled previously in a freezer for 20 minutes. The glass mold was covered and remained in the freezer until the prepared mixture froze (about 30 minutes). The frozen slab was then easily pried loose with a cold spatula; transferred onto a wire screen; and kept in the freezer for two days. The frozen slab was dried for an additional two days at room temperature in a dessicator under house vacuum.

Dye Release from the Polymeric Matrix

The dried slab was weighed and cut into nine small pieces. Each piece was weighed and placed in a test tube containing 10 mL 0.015M phosphate buffer, pH=7. These test tubes were shaken continuously at 50 rpms and kept at room temperature. Periodically, the dye-containing polymer pieces were transferred with forceps into test tubes containing fresh buffer. During the transfers, excess solution on the matrix surface was removed by gentle blotting on a tissue. The concentration of HPTS in the test tubes was determined by UV absorption at 405 nm.

Results

The construction of the fiber optic sensor is a critical element in its performance. Prior to the creation of the pH sensor design shown in FIG. 2, an earlier prototype sensor was designed with the polymeric matrix placed within the interior of the conduit member 50. Disadvantages associated with this arrangement were readily apparent. When the polymeric matrix was immediately below the fiber tip, the emerging light from the fiber strand was reflected by the polymeric matrix surface; and part of this reflected light reentered the fiber strand resulting in a systematic error in the signal. Therefore, a longer length sensing region was employed to minimize this back reflected light. This longer-length configuration, however, resulted in longer sensor response times. Another disadvantage with this earlier design was the buildup of a large concentration gradient of released dyes around the polymeric matrices. This concentration gradient constantly changed with time, causing instability even in the ratio measurement.

The sensor construction that overcame these drawbacks and problems was prepared by placing the polymeric matrices in a reservoir chamber section above the fiber tip. In this way, reflected light from the polymeric matrices was not a problem. In addition, variation in the concentration gradient of the dyes around the fiber tip was found to be minimal. An additional advantage of this configuration is the ability to enlarge the polymer reservoir section, thus, making the sensor last longer.

Figure 3:
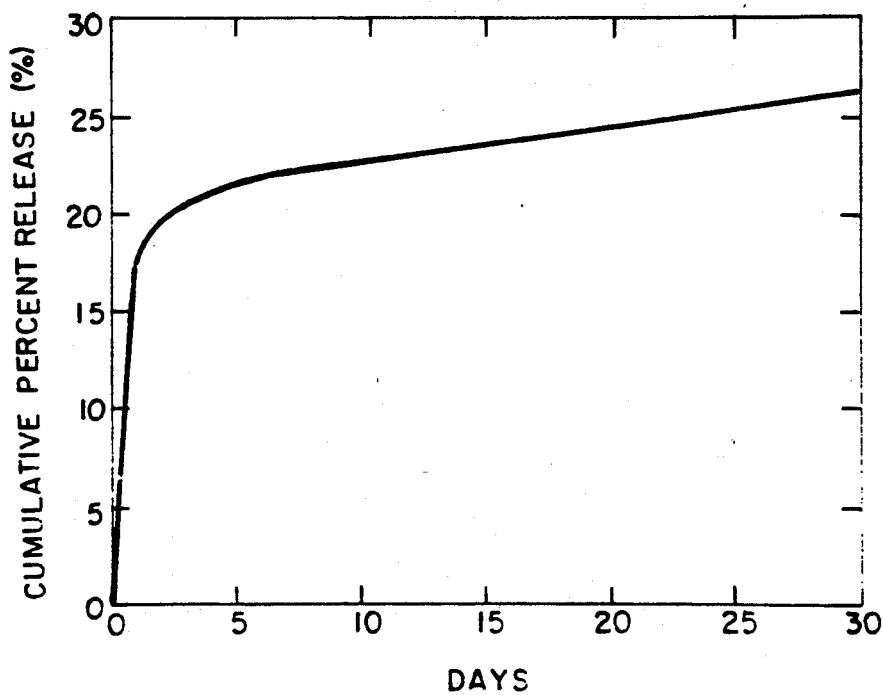
FIG. 3 is a graph illustrating the release rate of HPTS from a polymer matrix as determined by measuring ultraviolet absorption at 405 nanometers.

Based on the results of Langer et al. for incorporation of biologically active materials, [J. Pharm. Sci. 69:265-270 (1988)], an optimal total dye loading of 33% was used. Above this percentage loading, a rapid release of dye was observed—probably resulting from the higher porosity of the polymeric matrix—and facilitating the rapid diffusion of the dye out of the matrix. The fiber optic sensor containing both HPTS and SR640 in the polymeric matrix employed a one to one ratio of the two dyes; no experiments were performed to optimize the dye ratio in the polymer. This ratio was sufficient to obtain good sensitivity for pH measurements. The results of total HPTS release from the polymeric matrix are shown in FIG. 3 in which the concentration of HPTS was determined by measuring UV absorption at 405 nm. The initial rapid release was presumably due to HPTS dissolution from the polymeric surface. After this initial rapid release period, the release of HPTS became constant and continued for an extended period.

Figure 4:
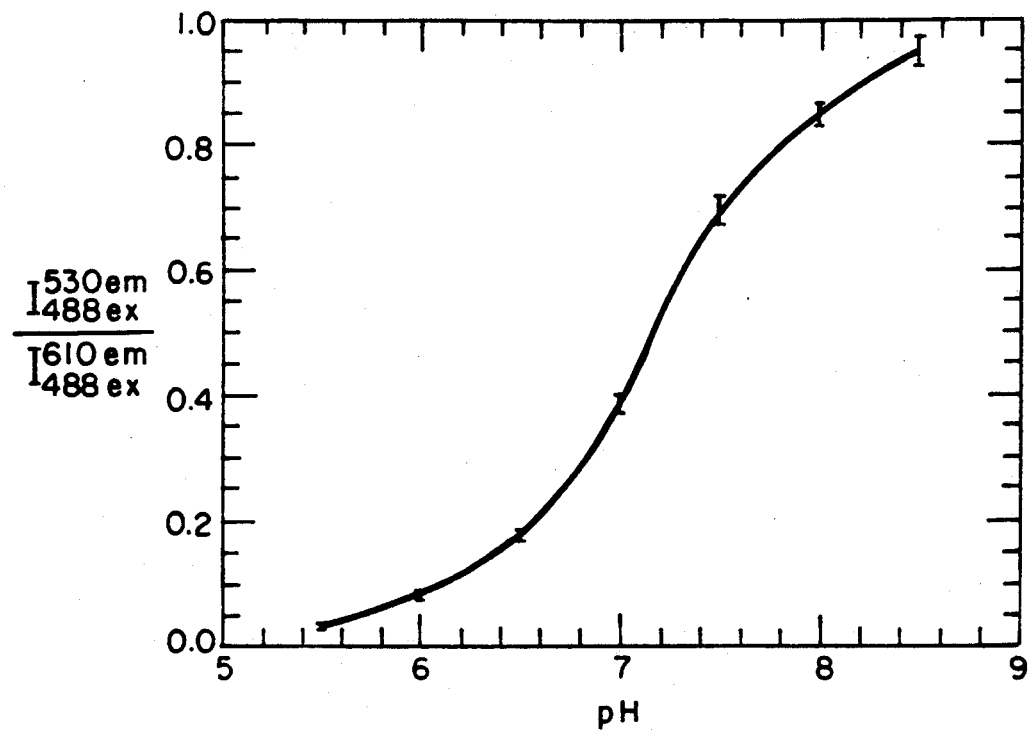
FIG. 4 is a graph illustrating the fluorescent emissions produced using excitation wavelengths of 405 and 450 nanometers as a function of changes in pH.

The sensor containing HPTS alone produced the pH data shown in FIG. 4. Two excitation wavelengths at 405 nm and 450 nm are used to excite the acid and base forms of HPTS respectively. Both forms of the dye emit light energy at 515 nm. As shown by the data of Table III, the measured emission intensity ratio is insensitive to the source intensity or the amount of HPTS in the sensing region at the time of measurement. In comparison, Table IV contains data of an HPTS sensor tested over a period of 38 days. On each day of measurement, the concentration of HPTS in the sensor was different and produced changing absolute readings of fluorescence intensities; however, the measured ratios always remained constant. The useful concentration range of HPTS in the sensor was found to be $10^{-4}M$ to $10^{-6}M$ as determined from standard solutions of HPTS. At concentrations below $10^{-6}M$, the ratio varies due to the relatively high background readings of the instrument. At concentrations above $10^{-4}M$, the intensity of fluorescence is too high to be readable on the photon counting detector. Therefore, the intensity ratio was measured only when the direct intensity readings exceeded 30 kcps (thousand photon counts per second) in order to minimize experimental deviation. From these data, pH values in the range of 5.5 to 8.0 can be measured with a minimum precision of ±0.07 pH units.

TABLE III

EFFECT OF SOURCE INTENSITY VARIATION
([HPTS] = $10^{-5}$1 M, pH = 8)

| CURRENT (amps) | A (kcps) | B (kcps) | RATIO (A/B) |
|---|---|---|---|
| 4 | 41.5 | 164 | 0.253 |
| 5 | 68.5 | 279 | 0.246 |
| 6 | 70.0 | 275 | 0.255 |

A. $ex$ = 405 nm; $em$ = 515 nm.
B. $ex$ = 450 nm; $em$ = 515 nm.

TABLE IV

FLUCTUATION OF HPTS SENSOR
AT pH 6.5 (Representative Data)

| TIME (days) | A (kcps) | B (kcps) | RATIO (A/B) |
|---|---|---|---|
| 7 | 191.5 | 57.5 | 3.33 |
| 18 | 367 | 110 | 3.34 |
| 22 | 142 | 42 | 3.38 |
| 28 | 417 | 123 | 3.39 |
| 38 | 677 | 201 | 3.37 |

A. $ex$ = 405 nm; $em$ = 515 nm.
B. $ex$ = 450 nm; $em$ = 515 nm.

Figure 5:
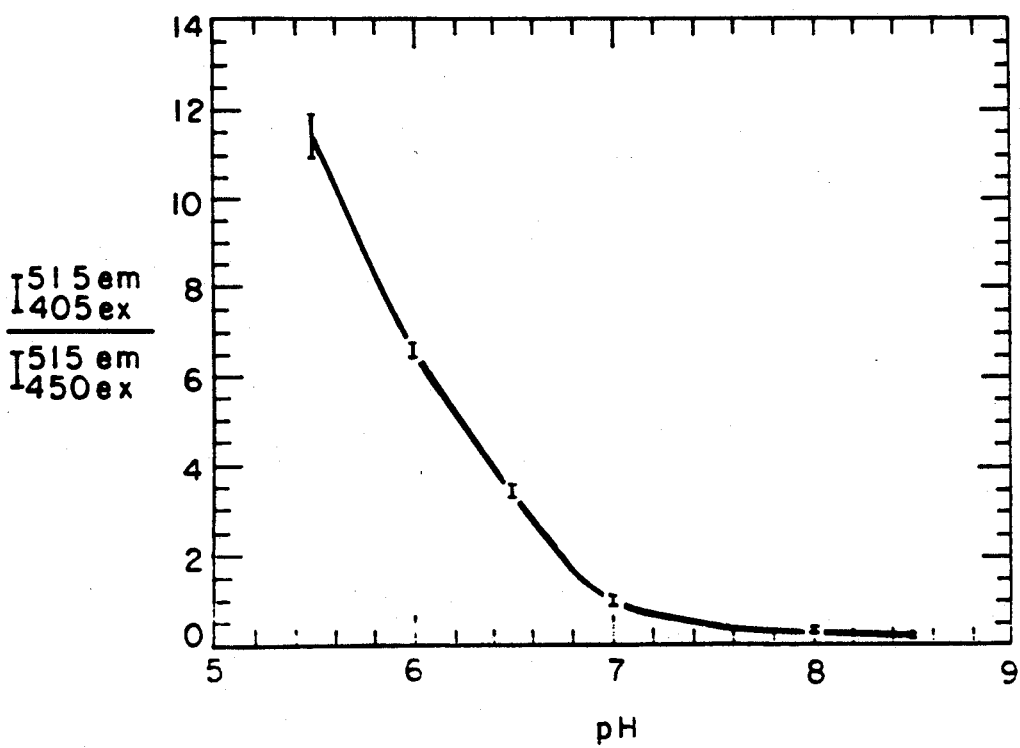
FIG. 5 is a graph illustrating the emission signals observed at 530 and 610 nanometers produced using laser excitation at 488 nanometers for two dyes as a factor of changes in pH values.

The second experimental series employed a mixture of HPTS and SR640 in the EVA polymeric matrix and produced the reversed intensity ratio vs. pH response curve shown in FIG. 5. Signal was produced with laser excitation at 488 nm; observations of emitted light were made at 530 and 610 nm. In this case, the release rate of the two dyes is critical since SR640 serves only as an internal reference; and variations in the release rate of the dyes would cause significant changes in the accuracy of the ratios. Therefore, before entrapping both dyes into the EVA polymer, they were dissolved in water and thoroughly mixed; water was then removed by lyophilization. With premixing, the dyes should be uniformly incorporated into the polymer and be released at virtually the same rate. However, the precision (±0.1 pH units) of this method in the pH range of 5.5 to 8.0 is not as good as the sensor which uses HPTS alone. On the other hand, the use of a single excitation wavelength in this sensor offers the potential for a simpler instrument design for field applications.

The response time per pH unit change of a sensor is a function of its design and the conditions of the solution being measured. As shown by Table V, stirring greatly enhanced the rate for establishing equilibrium between the analyte solution and solution inside the sensor; the response time decreased by nearly an order of magnitude (from 3 hours to 0.33 hour). When the hole diameter in the sensing region was enlarged from 0.25 to 0.36 mm, the response time decreased by more than 50% (from 0.67 hours to 0.25 hours). Furthermore, shortening the sensing region length by half decreased the response time by 33% (from 3 hours to 2 hours). The response time of this type of sensor is longer than for other pH sensors with immobilized reagents on the fiber tip. However, this response time is acceptable when sensors of this type are used in remote sensing applications for extended periods of time. These fiber optic sensors have worked in the laboratory for more than three months without any change in sensitivity or precision.

TABLE V

RESPONSE TIME OF HPTS SENSORS (hrs/pH unit)

| | SENSING LENGTH | | | |
|---|---|---|---|---|
| | 3 mm | | 6 mm | |
| HOLE DIAMETER | a | b | a | b |
| 0.25 mm | 0.67 | 4 | 1 | 6 |
| 0.36 mm | 0.25 | 2 | 0.33 | 3 | a. Data shown were measured with stirring.
b. Data shown were measured without stirring.

The present invention is not to be restricted in form nor limited in scope except by the claims appended hereto.

What is claimed is:

1. A fiber optic sensor for performing optical determinations of a plurality of test fluids, said sensor comprising;

a housing with a securing means to hold a fiber optic strand, said housing comprising a reservoir chamber of fixed configuration and interior spatial volume comprised of at least one side wall and having at least one open portal accessing said interior spatial volume;

at least one polymeric matrix comprising a fluid contact positioned within said interior spatial volume of said reservoir chamber, said polymeric matrix comprising a fluid erodible, continuous release polymer and a sustained release reagent formulation above to react with a molecule of interest in each of the test fluids;

a fiber optic strand positioned proximal to said erodible polymeric matrix within said reservoir chamber, said fiber optic strand being able to convey light energy into and out of said interior spatial volume of said reservoir chamber; and a conduit member of fixed dimensions and shape in fluid flow communication with said portal of said reservoir chamber, said conduit member being comprised of at least one side wall, at least one aperture perforating said wall, and a perforated internal volume in flow communication with said interior spatial volume of said reservoir chamber.

2. The fiber optic sensor as recited in claim 1 wherein said reagent formulation is selected from the group consisting of indicator compounds and dyes.

3. The fiber optic sensor as recited in claim 1 wherein said reagent formulation is selected from the group consisting of labelled immunological and immunochemical compositions.

4. The fiber optic sensor as recited in claim 1 wherein said reagent formulation is selected from the group consisting of enzyme system components and compositions.

5. The fiber optic sensor as recited in claim 1 wherein said continuous release polymer is a polyanhydride.

6. The fiber optic sensor as recited in claim 1 wherein said continuous release polymer is a vinyl polymer.

7. The fiber optic sensor as recited in claim 1 wherein said continuous release polymer is a polyacrylamide.

8. A fiber optic apparatus for performing optical determinations of a plurality of test fluids, said apparatus comprising:
   a fiber optical sensor comprised of:
   (i) a housing with a securing means to hold a fiber optic strand, said housing comprising a reservoir chamber of fixed configuration and interior spatial volume,
   (ii) at least one polymeric matrix erodible by repetitious fluid contact positioned within said interior spatial volume of said reservoir chamber, said polymeric matrix comprising a fluid erodible continuous release polymer and a sustained release reagent formulation able to react with a molecule of interest in each of the test fluids,
   (iii) a fiber optic strand positioned proximal to said erodible polymeric matrix within said reservoir chamber, said fiber optic strand being able to convey light energy into and out of said interior spatial volume of said reservoir chamber, and
   (iv) a conduit member for allowing each of the test fluids into and out of said interior spatial volume of said reservoir chamber wherein said conduit member comprises at least one side wall, at least one aperture perforating said wall, and a perforated internal volume in flow communication with said interior spatial volume of said reservoir chamber;
   a source of light energy;
   means for conveying light energy from said source to said fiber optic sensor;
   means for detecting light energy; and
   means for conveying light energy from said fiber optic sensor to said detecting means.

9. The fiber optic sensing apparatus as recited in claim 8 further comprising a computer control and data acquisition system.

10. The fiber optic sensing apparatus as recited in claim 8 wherein said light energy is in the ultraviolet light range.

11. The fiber optic sensing apparatus as recited in claim 8 wherein said light energy is in the visible light range.

12. A method for making optical determinations of a plurality of test fluids, said method comprising the steps of:
   obtaining a fiber optic sensor comprised of:
   a housing with a securing means to hold a fiber optic strand, said housing comprising a reservoir chamber of fixed configuration and interior spatial volume,
   (ii) at least one polymeric matrix erodible by repetitious fluid contact positioned within said interior spatial volume of said reservoir chamber, said polymeric matrix comprising a fluid erodible continuous release polymer and a sustained release reagent formulation able to react with a molecule of interest in each of the test fluids,
   (iii) a fiber optic strand positioned proximal to said erodible polymeric matrix within said reservoir chamber, said fiber optic strand being able to convey light energy into and out of said interior spatial volume of said reservoir chamber, and
   (iv) a conduit member for allowing each of the test fluids into and out of said interior spatial volume of said reservoir chamber wherein said conduit member comprises at least one side wall, at least one aperture perforating said wall, and a perforated internal volume in flow communication with said interior spatial volume of said reservoir chamber;
   introducing each of the test fluids into said interior spatial volume of said reservoir chamber via said conduit member such that said polymeric matrix partially erodes and continuously releases said reagent formulation for mixture and reaction with said molecule of interest within each of said introduced test fluids;
   conveying light energy to said fiber optic sensor such that said light energy interacts with each of said reaction mixtures comprised of released reagent formulation and said molecule of interest within said reservoir chamber; and
   detecting the light energy conveyed by said fiber optic sensor after light interaction with each of said reaction mixtures comprised of released reagent formulation and said molecule of interest.

* * * * *